(12) United States Patent
Matsumoto et al.

(10) Patent No.: US 6,294,056 B1
(45) Date of Patent: Sep. 25, 2001

(54) DISTILLATION METHOD AND DISTILLATION APPARATUS

(75) Inventors: Yukihiro Matsumoto, Kobe; Kazukiyo Arakawa, Himeji; Osamu Dodo, Hyogo-ken; Hiroo Iwato, Himeji; Mamoru Takamura, Takasago, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/253,036

(22) Filed: Feb. 19, 1999

(30) Foreign Application Priority Data

Feb. 20, 1998 (JP) .................................................. 10-038857

(51) Int. Cl.⁷ ................................ B01D 3/14; C07C 51/44
(52) U.S. Cl. ...................... 203/90; 203/91; 203/DIG. 21; 202/158; 202/236; 261/97; 261/114.5; 562/600
(58) Field of Search .................................. 203/100, 2, 8, 203/3, 90, 91, DIG. 21; 208/48 AA; 585/5; 202/160, 236, 158; 562/600; 159/43.1; 261/114.5, 97, 98, 113, 114.4

(56) References Cited

U.S. PATENT DOCUMENTS

| | | | |
|---|---|---|---|
| 3,717,553 | * | 2/1973 | Otsuki et al. .................... 202/158 |
| 3,988,213 | * | 10/1976 | Yoshida et al. ........................ 203/9 |
| 4,442,048 | * | 4/1984 | Abernathy et al. ............... 261/114.1 |
| 4,444,696 | | 4/1984 | Harper et al. . |
| 4,574,007 | * | 3/1986 | Yearout et al. ...................... 202/158 |
| 4,816,191 | * | 3/1989 | Bervan et al. ......................... 261/97 |
| 5,645,770 | * | 7/1997 | McNulty et al. ...................... 261/97 |

FOREIGN PATENT DOCUMENTS

| 0 753 521 | 1/1997 | (EP) . |
|---|---|---|
| 2 092 175 | 8/1982 | (GB) . |

* cited by examiner

Primary Examiner—Virginia Manoharan
(74) Attorney, Agent, or Firm—Oblon, Spivak, McClelland, Maier & Neustadt, P.C.

(57) ABSTRACT

In a method for distilling (meth)acrylic acid and/or (meth) acrylic ester, the method has the step of uniformly distributing a supply liquid in a distillation tower over an entirety of a horizontal cross sectional area in the distillation tower. A distillation apparatus for distilling (meth)acrylic acid and/or (meth)acrylic ester in a distillation tower has a supply element for supplying the supply liquid into the distillation tower. The supply element is formed with at least two supply ports through which the liquid is supplied into the distillation tower.

5 Claims, 5 Drawing Sheets

DISTILLATION METHOD AND DISTILLATION APPARATUS

BACKGROUND OF THE INVENTION

This invention relates to a method and an apparatus for distilling (meth)acrylic acid and/or (meth)acrylic ester in a distillation tower.

Distillation is an operation in which a raw liquid composed of two or more liquids in a mixed manner each having a different boiling point is heated for vaporization and the gas (or vapor) mainly composed of a component having a lower boiling point is condensed to separate the components of the mixture of liquids. In the case where the relative volatility between the components is great, the separation of the components is easy. However, there comes a problem that, in a normal state, the components cannot be separated with a desired concentration by merely vaporizing and condensing part of the mixture of liquids. Accordingly, it is a general practice in the art of distillation that part of the condensed liquid is returned (refluxed) from the top of the distillation tower while passing a tray or a surface of a packing provided in the tower to render the gas rising up through the distillation tower into contact with the reflux liquid returning from the top of the tower in an adequate manner so as to withdraw the component having a lower boiling point through the top of the distillation tower while withdrawing the component having a higher boiling point through the bottom of the distillation tower. The efficiency (distillation performance) of the distillation tower can be theoretically calculated according to the specification of the tower, the flow rate of the liquid and the gas to be supplied through the tower, and the property thereof.

If, however, the distributing ability of a liquid to be supplied into the distillation tower (hereinafter, also referred to as "supply liquid") such as a raw liquid and a reflux liquid is low, the supply liquid unevenly flows through the distillation tower. Accordingly, it takes a plurality of trays when the apparatus/method adopts the tray tower, or a packing with a thickness of several ten millimeters is required when the apparatus/method adopts the packed tower system to evenly distribute the liquid.

Namely, in the conventional method and apparatus, a certain level of distillation performance that would have been obtained according to the theory could not be obtained occasionally. Especially, if the diameter of the distillation tower is large, or the surface tension of the supply liquid is great, or the viscosity of the supply liquid is high, or the supply liquid has a property that the liquid is easily separated into two liquid phases of oil phase and water phase, a problem has been pointed out that the liquid is liable to unevenly pass through the distillation tower, which would lower the distillation efficiency. Especially, the prior art apparatus/method has suffered from a problem that the distillation efficiency is gradually lowered in the case of distilling (meth)acrylic acid and/or (meth)acrylic ester.

FIG. 1 is a cross sectional view exemplifying a tray tower 10 which is generally used in the prior art when distilling (meth)acrylic acid and (meth)acrylic ester (hereinafter, also simply referred to as "(meth)acrylic acid" as a general term for (meth)acrylic acid and (meth)acrylic ester). In this embodiment, described is a case where a raw liquid in which (meth)acrylic acid is contained as a main component and acetic acid is contained as an impurity is used for distillation. The raw liquid is supplied into the distillation tower 10 through a line $L_1$. Acetic acid having a lower boiling point rises up through the distillation tower 10 while being vaporized by heating, and is introduced into condensing means 20 via the top of the distillation tower 10 through a line $L_2$. After condensation by the condensing means 20, the condensed liquid is drawn out through a line $L_3$.

On the other hand, (meth)acrylic acid, having a higher boiling point, is drawn out from the bottom of the distillation tower 10 to a next step through a line $L_4$. Part of a refined liquid obtained by the above distillation is returned to the distillation tower 10 via a reboiler 30 through a line $L_5$. Since the condensed liquid by the condenser 20 contains (meth)acrylic acid as well as acetic acid (impurity), part of the condensed liquid is returned into the distillation tower 10 through a line $L_6$ as a reflux liquid to improve collecting efficiency of (meth)acrylic acid. After subject to gas-liquid contact in the distillation tower 10, (meth)acrylic acid in the reflux liquid flows down onto the bottom of the distillation tower 10 and is drawn out to the next step.

Since (meth)acrylic acid is a compound liable to be polymerized quite easily, it is a general practice to add a polymerization inhibitor such as hydroquinone and phenothiazine to the raw liquid and the reflux liquid. Also, there has been adopted a method for supplying oxygen through a line $L_7$ to the bottom portion of the distillation tower 10 to suppress polymerization.

Despite of the above countermeasures, however, polymerization of (meth)acrylic acid cannot be completely prevented. Containment of polymerized matters in the distillation tower 10 lowers purification performance in the distillation tower 10. Accordingly, what frequently happened was to suspend operation of the distillation tower 10 for removing the polymerized matters accumulated in the distillation tower 10.

SUMMARY OF THE INVENTION

In view thereof, an object of this invention is to provide a method and an apparatus for distilling (meth)acrylic acid and/or (meth)acrylic ester that enables distillation of supply liquid with high purification efficiency for a long operating time, while preventing polymerization of (meth)acrylic acid in the distillation tower.

To achieve the above object, an aspect of this invention is directed to a method for distilling (meth)acrylic acid and/or (meth)acrylic ester in a distillation tower, comprising the step of uniformly distributing a supply liquid to be supplied into the distillation tower over an entirety of a horizontal cross sectional area in the distillation tower to prevent polymerization of (meth)acrylic acid in the distillation tower.

According to the distillation method of this invention, the supply liquid may include a raw liquid before distillation, a reflux liquid which is returned into the distillation tower after condensation outside the distillation tower, and a refined liquid obtained after the distillation.

Preferably, according to the distillation method of this invention, at least one of the supply liquids may be supplied into the distillation tower through at least two supply ports.

More preferably, according to the distillation method of this invention, at least one of the supply liquids may be supplied into the distillation tower in a spraying manner.

In the case where the distillation tower is a tray tower, the concentration of a composition in a liquid existing at any location of a tray immediately below the supply port may vary within the range of ±30% of the average concentration of the liquid on the tray. It may be preferable to set a pressure loss at the supply port of the liquid at 50 mmH$_2$O or more so as to uniformly distribute the liquid.

Another aspect of this invention is directed to an apparatus for distilling (meth)acrylic acid and/or (meth)acrylic ester in a distillation tower comprising: supply means for supplying at least one of supply liquids including a raw liquid, reflux liquid, and a refined liquid into the distillation tower, the supply means including at least two supply ports through which the liquid is supplied into the distillation tower.

Preferably, the supply port may be provided with a pressure loss generator (e.g., an orifice plate).

More preferably, the supply means for supplying at least one of the supply liquids including a raw liquid, a reflux liquid, and a refined liquid may include an atomizer.

The above and other objects, features and advantages of the present invention will become more apparent upon a reading of the following detailed description and drawings.

DETAILED DESCRIPTION OF THE INVENTION

Figure 2:
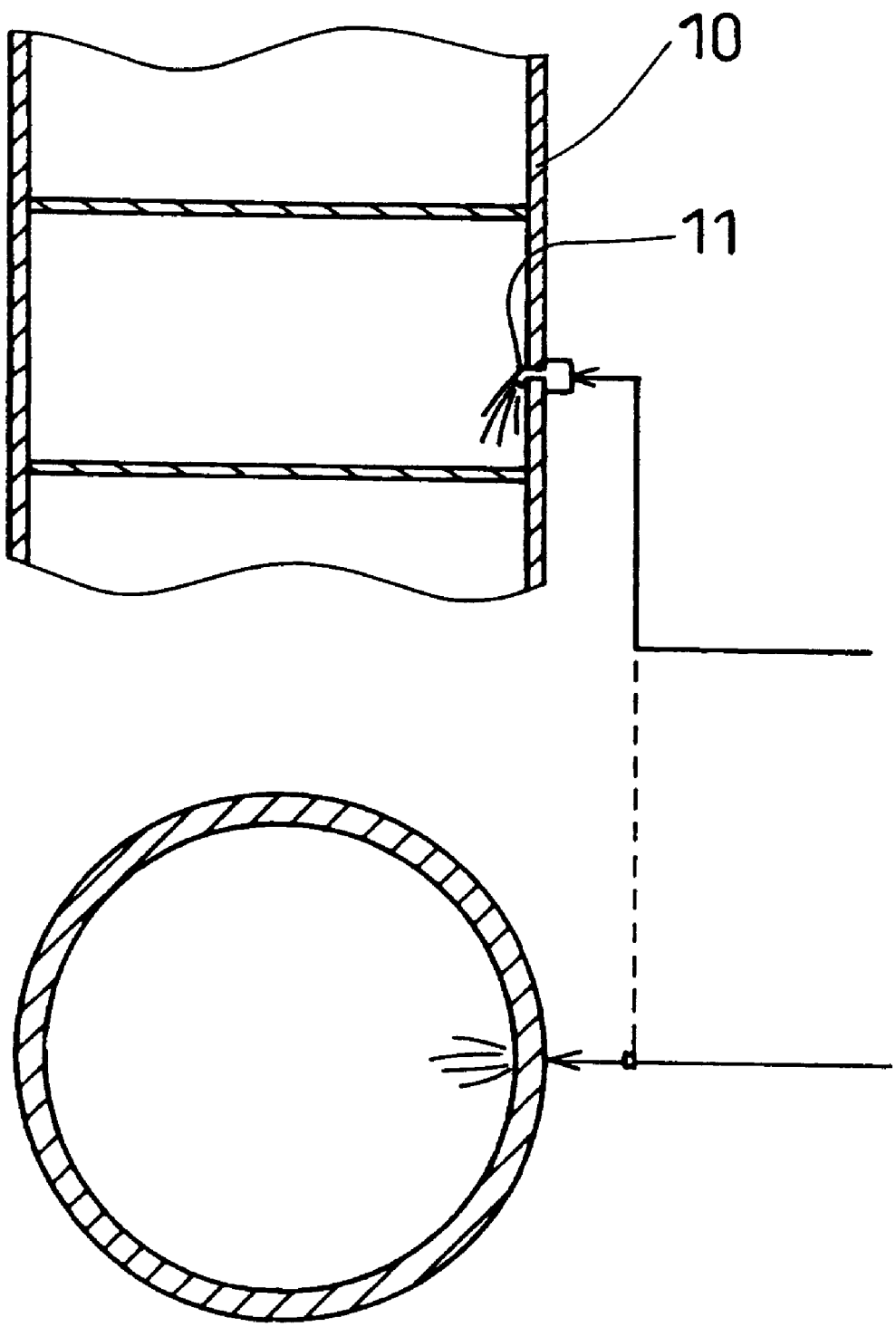
FIG. 2 is a schematic diagram showing a manner of supplying a liquid according to the prior art method.

Before describing a preferred embodiment of this invention, briefly described is a manner of supplying a liquid according to prior art method with reference to FIG. 2.

FIG. 2 is a partially cross sectional view of a distillation tower of prior art for distilling (meth)acrylic acid and (meth)acrylic ester. In FIG. 2, a nozzle 11 is provided at a side wall of the distillation tower 10 to supply a raw liquid into the distillation tower 10. Also, another nozzle (not shown) is provided at the distillation tower 10 to supply a reflux liquid and a refined liquid to be returned into the distillation tower 10.

As a result of an investigation of a cause that would lead to polymerization of (meth)acrylic acid during distillation, the inventors (applicants) of this application found out that a supply liquid such as a raw liquid and a reflux liquid is unevenly supplied into the distillation tower 10, namely, the problem resides in the manner of supplying the liquid.

Specifically, when distilling (meth)acrylic acid and (meth)acrylic ester in the distillation tower 10, the concentration of a composition in the liquid in the distillation tower 10 varies, and accordingly, the polymerization inhibitor in the supply liquid is unevenly distributed in terms of liquid phase. Further, gas unevenly flows in terms of gaseous phase. Thereby, distributing performance of oxygen supplied into the distillation tower 10 for the purpose of suppressing polymerization is lowered.

In addition, since the liquid flows through the distillation tower 10 unevenly, there occur various problems such that the temperature in the distillation tower unevenly rises at several locations, the liquid remains on the surface of the parts inside the distillation tower 10, and dried-up locations appear in the distillation tower 10. In this way, locations appear here and there inside the distillation tower 10 where polymerization is liable to occur. If polymerized matters are generated, it is required to suspend operation of the distillation apparatus so as to remove the polymerized matters accumulated in the distillation tower 10. In particular, as the diameter of the distillation tower increases, polymerization likely occurs. Further, in the case where the supply liquid has a high viscosity, a large surface tension, and a property that the liquid is easily separated into two phases (oil phase and water phase), there cannot be avoided a phenomenon that the liquid unevenly flows through the distillation tower, which would conspicuously lower the distillation efficiency.

In order to solve the above problem, according to the distillation method of this invention, the supply liquid is uniformly supplied (distributed) onto an entirety of a horizontal cross sectional area in a distillation tower to prevent polymerization of (meth)acrylic acid in the supply liquid inside the distillation tower. In order to supply the liquid as uniformly as possible, it may be preferable to supply at least one of the supply liquids through at least two supply locations (ports) or in a spraying manner.

The more the supply locations are provided for any kind of supply liquid, the better result is obtained. In this embodiment, providing four or more supply ports is preferable. It should be appreciated, however, that what is essentially important in this invention is to uniformly flow the liquid through the distillation tower. Accordingly, it may be preferable to set a plurality of supply ports in a symmetric relation with respect to a center of axis of the distillation tower.

Further, it may be preferable to set the flow rate of supply liquid to be supplied through each supply port at an equivalent value as possible. In order to suppress variation of the flow rate, it may be preferable to provide an orifice plate, a valve, a reducer or its equivalent at a specified position in the supply port so as to set a pressure loss at the supply port at 50 mmH$_2$O or more.

In the case of providing an orifice plate, it may be preferable to set the value of pressure loss within the range of 100 to 200 mmH$_2$O. It should be noted, however, that the effect of suppressing the variation of flow rate cannot be expected further if the pressure loss is too large. Accordingly, it may be preferable to set the upper limit of pressure loss at 500 mmH$_2$O. In the case of using a spray device at the supply port, the value of pressure loss is usually within the range of 3000 to 10000 mmH$_2$O.

Figure 3:
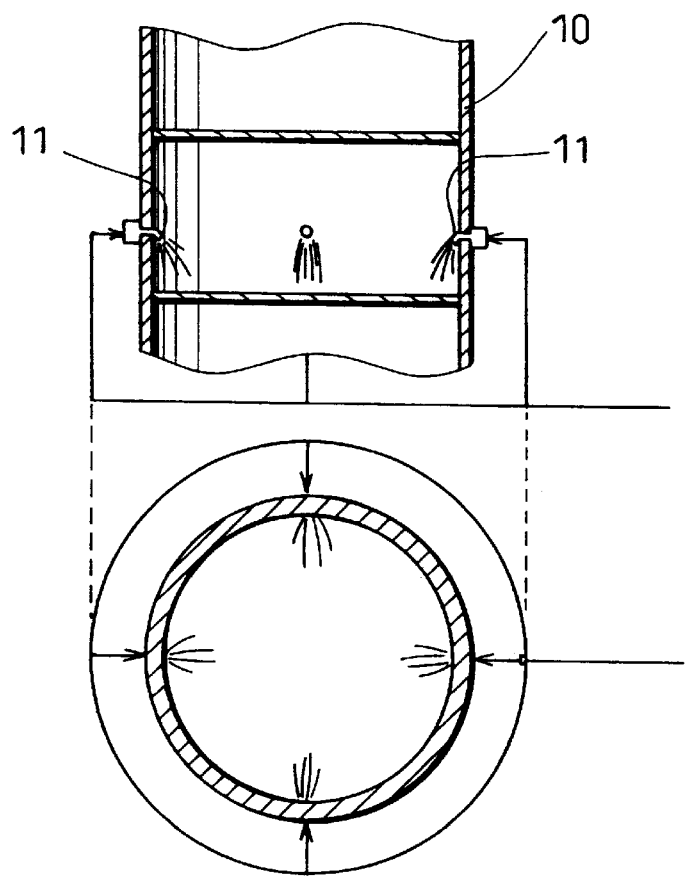
FIG. 3 is a schematic diagram partially showing a method of supplying a liquid according to this invention.
Figure 4:
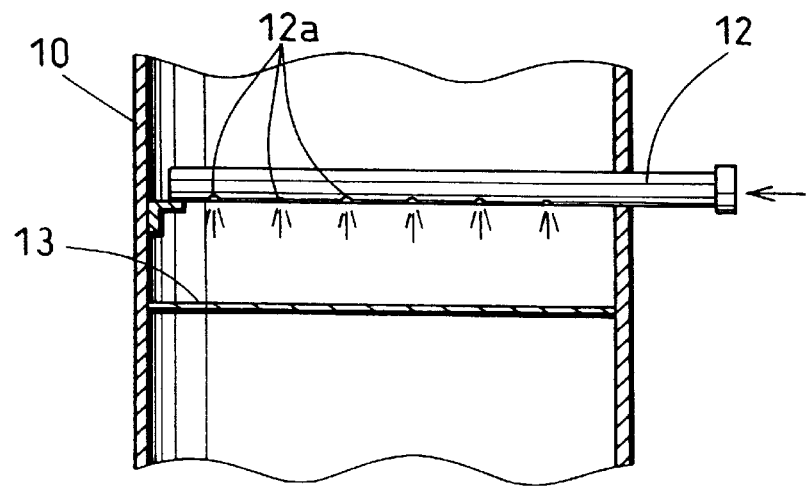
FIG. 4 is a schematic diagram partially showing the method of supplying a liquid as an altered arrangement according to this invention.

FIG. 3 is a diagram showing a manner of supplying a raw liquid through a plurality of nozzles 11 provided in a side wall of a distillation tower 10 according to this invention. FIG. 4 is a diagram showing a manner of sprinkling the liquid onto a sieve tray 13 through a number of supply holes 12a formed in a distributor pipe 12 inside the distillation tower 10 according to this invention. In FIGS. 3 and 4, providing a plurality of supply holes 12a and nozzles 11 enables uniform distribution of the liquid onto the tray 13 to improve distributing ability of the supply liquid.

Figure 5:
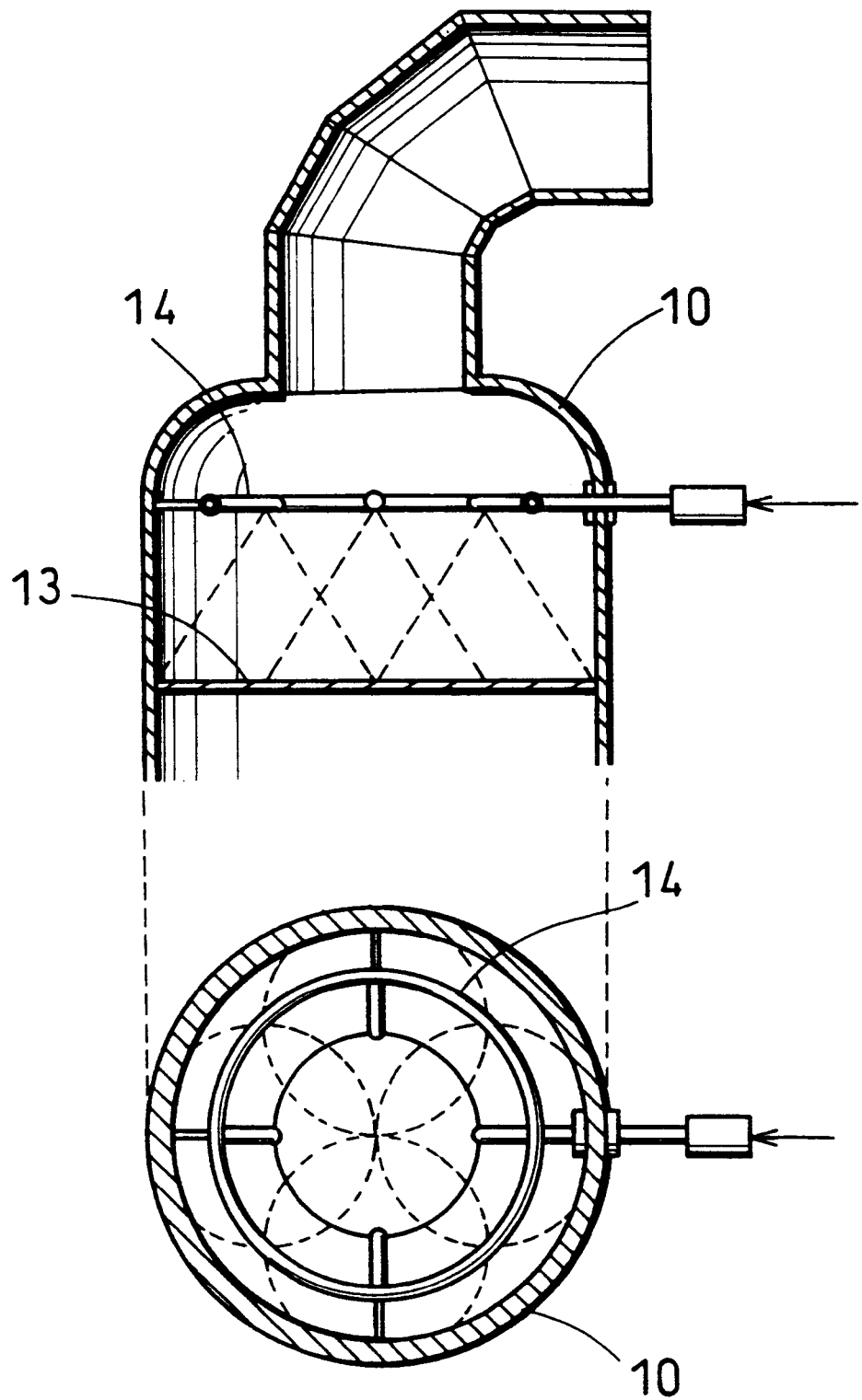
FIG. 5 is a schematic diagram partially showing the method of supplying a liquid according to this invention.

FIG. 5 is a diagram showing an example of supplying a reflux liquid through the top of the distillation tower 10.

In FIG. 5, the reflux liquid is sprayed onto the tray 13 through four supply ports (shower nozzles) formed in a distributor pipe 14. When supplying the reflux liquid through the top of the distillation tower 10, it is likely that a so-called "entrainment" phenomenon is accompanied in which the liquid is splashed against gas floating around the top of the distillation tower 10. Accordingly, it is preferable to spray the liquid downward, as shown in FIG. 5, to prevent the entrainment as much as possible.

On the other hand, polymerization is likely to occur on the surface of parts at the top of the distillation tower 10 such as a head, a vapor outlet pipe and so on. Accordingly, in this case, it may be preferable to spray the liquid upward to prevent polymerization. Further, it may be preferable to prepare a spray device capable of spraying droplets of the liquid having a relatively large diameter to prevent occurrence of the entrainment.

Figure 6:
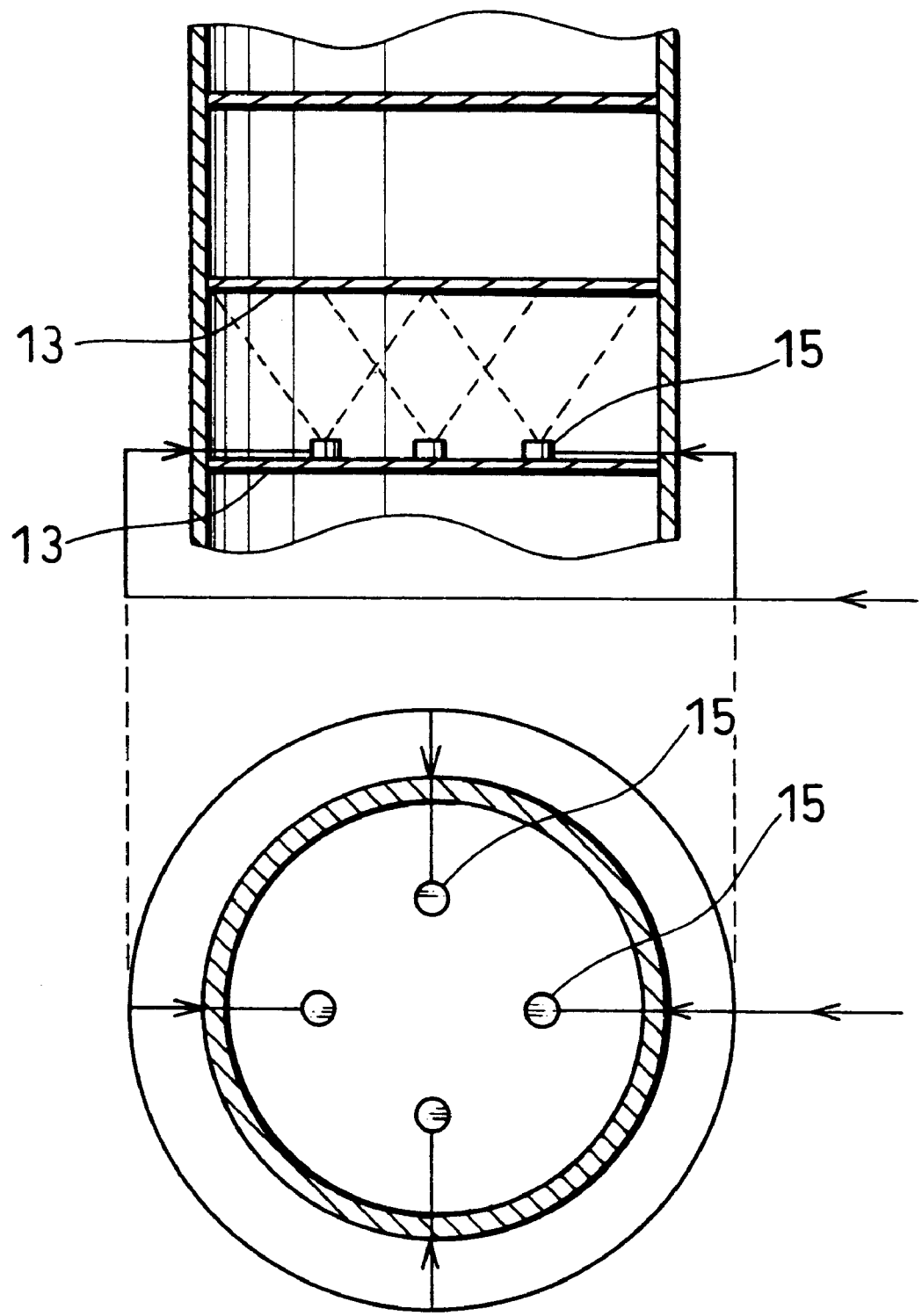
FIG. 6 is a schematic diagram partially showing the method of supplying a liquid as an altered arrangement according to this invention.

FIG. 6 is a diagram showing an altered arrangement of the method of supplying the supply liquid according to this invention. In FIG. 6, spray devices 15 are provided on the sieve tray 13 to supply the liquid in the form of mist. When the liquid is supplied through an intermediate portion of the distillation tower 10, where the sieve trays 13 are set at a relatively small height interval, and the distance between the spray device 15 and the sieve tray 13 (or a packing) is small, it is preferable to spray the liquid upward instead of downward spraying to improve the distributing performance of the liquid.

Further, it is preferable to set the composition of the supply liquid equal as much as possible at any portion of the liquid regardless of the type of supply liquid (raw liquid, reflux liquid, and refine liquid). Specifically, the concentration of a composition in a liquid existing at any location (surface) of the sieve tray 13 immediately below the supply port may be varied within the range of ±30% of the average concentration of the liquid on the sieve tray 13. More preferably, the variation is set within the range of ±20%.

One type of the supply liquid may be sprayed onto the sieve tray 13. However, it may be preferable to spray two or three types of the supply liquid onto the sieve tray 13 to attain uniform concentration of the composition (component) contained in the supply liquid to be supplied into the distillation tower 10.

According to this invention, even if the diameter of the distillation tower 10 is large, the supply liquid can be distributed uniformly into the distillation tower 10. Further, even if the supply liquid has a high viscosity and a large surface tension, gas-liquid contact efficiency is improved. Even if the supply liquid has a property such that the liquid is easily separated into two phases (oil phase and water phase), the supply liquid can be uniformly distributed.

Hereinafter, an example to realize the invention is described in detail. The following example is, however, merely one of the examples to realize the present invention. Accordingly, the invention should not be limited by the described example. It is to be understood that various changes and modifications on the design will be apparent to those skilled in the art without departing from the spirit and scope of the present invention.

EXAMPLE

Used was a distillation tower of a stainless steel (SUS316) internally provided with 50 sieve trays of a stainless steel (SUS316) having an inner diameter of 2200 mm. Acrylic acid was refined using this distillation tower according to the prior art method and the method of this invention. A liquid containing 96 weight % of acrylic acid and 2 weight % of acetic acid was used as a raw liquid. The raw liquid was supplied onto the tenth tray from the uppermost position in the distillation tower at the flow rate of 9200 kg/hr in which 50 ppm of hydroquinone was used as a polymerization inhibitor. A distillation (refinement) of the acrylic acid was conducted in the above distillation tower continuously for 30 days under the condition: at the tower top temperature 63° C., at the tower top pressure 40 mmHg absolute, the flow rate of the reflux liquid 8400 kg/hr, the concentration of hydroquinone in the reflux liquid 100 ppm, the flow rate of the liquid drawn through the top of the distillation tower 1200 kg/hr, and oxygen supply rate through the bottom of the distillation tower 10 Nm³/hr. After the distillation, the concentration of acetic acid at the bottom of the distillation tower was measured, the liquid at arbitrary eight points on the tray on which the raw liquid was supplied was collected, and the variation of the concentration of hydroquinone in the collected liquid was measured. Also, the distillation tower was put into disassembly after continuous operation of the apparatus for 30 days, and the amount of polymerized matters accumulated in the distillation tower was measured.

[Prior Art Method]

Figure 1:
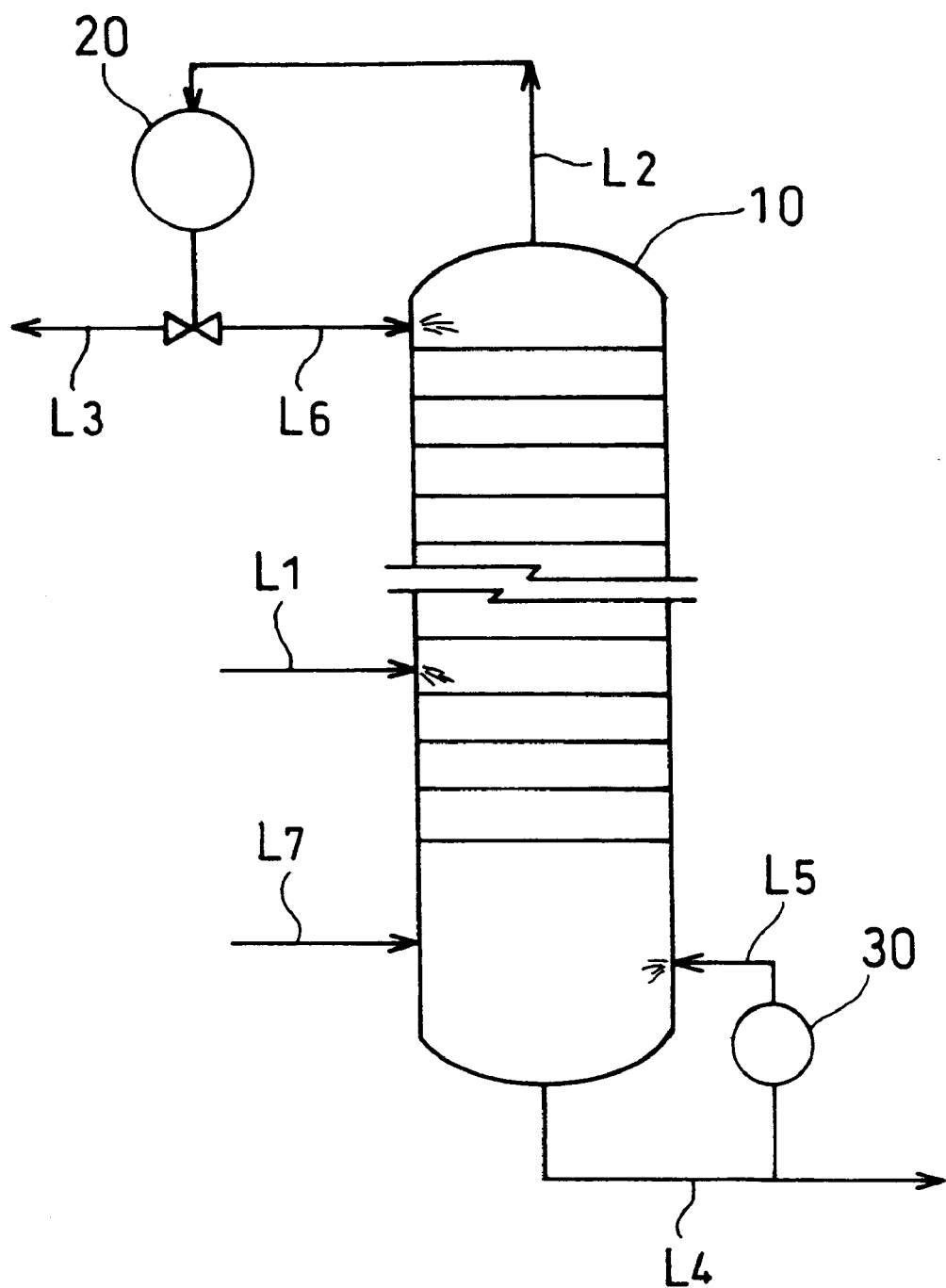
FIG. 1 is a schematic diagram showing a distillation method of the prior art.

The raw liquid and the reflux liquid were supplied through one supply port formed in the side wall of the distillation tower shown in FIGS. 1 and 2, and distillation was conducted under the above conditions for 30 consecutive days. As a result of the experiment, the concentration of acetic acid drawn through the bottom of the distillation tower was 1430 ppm, and the variation of the concentration of hydroquinone was within the range of −63 to +72% of the average concentration of the liquid on the tray. The amount of polymerized matters accumulated in the distillation tower was 15 kg.

Example 1 According to the Inventive Method

The raw liquid and the reflux liquid were supplied through four nozzles provided at the side wall of the distillation tower according to this invention in such a manner that the distribution ratio of the raw liquid to the reflux liquid is set at a certain value. An orifice plate was provided in each of the four nozzles. The liquid was supplied in a state that the pressure loss at the orifice plate was 150 mmH₂O, and distillation was conducted under the above condition for 30 consecutive days. As a result of the experiment, the concentration of acetic acid drawn through the bottom of the distillation tower was 850 ppm, the variation of the concentration of hydroquinone was in the range of −27 to +23% of the average concentration of the liquid on the tray, and the amount of polymerized matters accumulated in the distillation tower was 2 kg.

Example 2 According to the Inventive Method

The raw liquid was supplied in a similar manner as Example 1, and the reflux liquid was sprayed onto the tray through four supply ports as shown in FIG. 5. Distillation was conducted under the above condition for 30 consecutive days. As a result of the experiment, the concentration of acetic acid drawn through the bottom of the distillation tower was 120 ppm, the variation of the concentration of hydroquinone was in the range of −11 to +8% of the average concentration of the liquid on the tray, and the amount of polymerized matters accumulated in the distillation tower was 0.5 kg.

Example 3 According to the Inventive Method

The reflux liquid was supplied according to the method shown in FIG. 5, and the raw liquid was supplied according to the method shown in FIG. 6 in which the reflux liquid and the raw liquid were sprayed onto the tray through the respective four supply ports. Distillation was conducted under the above condition for 30 consecutive days. As a result of the experiment, the concentration of acetic acid drawn through the bottom of the distillation tower was 80 ppm, the variation of the concentration of hydroquinone was in the range of −2 to +3% of the average concentration of the liquid on the tray, and the amount of polymerized matters accumulated in the distillation tower was 0.1 kg.

The result of the above experiments is shown in Table 1.

TABLE 1

|  | concentration of acetic acid at tower bottom (ppm) | variation of concentration of hydroquinone (%) | amount of polymerized matter in tower (kg) |
| --- | --- | --- | --- |
| Prior Art Method | 1430 | −63 to +72 | 15 |
| Example 1 | 850 | −27 to +23 | 2 |
| Example 2 | 120 | −11 to +8 | 0.5 |
| Example 3 | 80 | −2 to +3 | 0.1 |

As mentioned above, it is obvious that distillation of supply liquid with high purification performance can be performed for a long operating time according to the method and apparatus of this invention, while preventing polymerization of (meth)acrylic acid in the supply liquid supplied into the distillation tower.

To sum up the above, according to the invention, provided is a method and an apparatus for distilling (meth)acrylic acid and/or (meth)acrylic ester that enables distillation of supply liquid with high purification performance for a long operating time while preventing polymerization of (meth)acrylic acid in the supply liquid.

Although the present invention has been fully described by way of example with reference to the accompanying drawings, it is to be understood that various changes and modifications will be apparent to those skilled in the art. Therefore, unless otherwise such change and modifications depart from the scope of the invention, they should be construed as being included therein.

What is claimed is:

1. A method for distilling (meth)acrylic acid and/or (meth)acrylic ester in a distillation tower having trays, which trays have a flat upper surface, wherein a plurality of openings are formed in each of the trays so that liquid and gas pass through the openings, the method comprising the step of uniformly distributing a supply liquid to be supplied into the distillation tower through a spraying device over an entirety of a horizontal cross sectional area in the distillation tower to prevent polymerization in the distillation tower, wherein the supply liquid is at least one of a raw liquid, a reflux liquid and a refined liquid, wherein at least one of the supply liquids is supplied into the distillation tower through at least two supply ports, and wherein a pressure loss at a supply port, where the liquid is supplied into the tower, of the supply liquid is at least 50 mmH$_2$O.

2. A method for distilling (meth)acrylic acid and/or (meth)acrylic ester in a distillation tower having trays, which trays have a flat upper surface, wherein a plurality of openings are formed in each of the trays so that liquid and gas pass through the openings, the method comprising the step of uniformly distributing a supply liquid to be supplied into the distillation tower through a spraying device over an entirety of a horizontal cross sectional area in the distillation tower to prevent polymerization in the distillation tower, wherein the supply liquid is at least one of a raw liquid, a reflux liquid and a refined liquid, wherein at least one of the supply liquids is supplied into the distillation tower through at least two supply ports, and wherein a concentration of a composition in a liquid existing at any location of a tray immediately below a supply port, where the liquid is supplied into the tower, varies within the range of ±30% for the average concentration of the liquid on the tray.

3. A distillation apparatus for distilling (meth)acrylic acid and/or (meth)acrylic ester in a distillation tower comprising:

supply means for supplying at least one of supply liquids including a raw liquid, a reflux liquid and a refined liquid into the distillation tower, the supply means including at least two supply ports through which the supply liquid is supplied into the distillation tower, wherein the supply port is provided with a pressure loss generator.

4. The distillation apparatus according to claim 3, wherein the pressure loss generator includes an orifice plate.

5. A distillation apparatus for distilling (meth)acrylic acid and/or (meth)acrylic ester in a distillation tower comprising:

supply means for supplying at least one of supply liquids including a raw liquid, a reflux liquid, and a refined liquid into the distillation tower, the supply means including a sprayer, wherein the supply means is provided with a pressure loss generator.

* * * * *

UNITED STATES PATENT AND TRADEMARK OFFICE
CERTIFICATE OF CORRECTION

PATENT NO.     : 6,294,056 B1
DATED          : September 25, 2001
INVENTOR(S)    : Yukihiro Matsumoto et al.

It is certified that error appears in the above-identified patent and that said Letters Patent is hereby corrected as shown below:

<u>Title page,</u>
Item [56], References Cited, please add the following:
-- OTHER PUBLICATIONS
Henry Z. Kister, Distillation Operation, pages 21- 83, "REFLUX AND INTERMEDIATE FEED INLETS FOR TRAY COLUMNS," 1990 --

Signed and Sealed this

Twenty-seventh Day of May, 2003

JAMES E. ROGAN
*Director of the United States Patent and Trademark Office*